United States Patent [19]

Jubran

[11] Patent Number: 5,284,812
[45] Date of Patent: Feb. 8, 1994

[54] THIAZOLO[5,4-D]THIAZOLE COLOR-FORMERS

[75] Inventor: Nusrallah Jubran, St. Paul, Minn.

[73] Assignee: Minnesota Mining and Manufacturing Company, St. Paul, Minn.

[21] Appl. No.: 817,386

[22] Filed: Jan. 6, 1992

[51] Int. Cl.$^5$ .............. B41M 5/136; B41M 5/165
[52] U.S. Cl. .................. 503/201; 428/402.2; 428/402.21; 503/202; 503/213; 503/215; 503/217
[58] Field of Search .......... 503/202, 217, 201, 213, 503/215; 106/21 R; 428/402.21, 402.2

[56] References Cited

U.S. PATENT DOCUMENTS

| | | | |
|---|---|---|---|
| 3,250,617 | 5/1966 | Sawdey | 96/55 |
| 3,326,672 | 6/1967 | Dressler et al. | 8/31 |
| 3,457,231 | 7/1969 | Sonnenfeld | 260/72 |
| 3,481,759 | 12/1969 | Ostlie | 117/36.2 |
| 3,516,941 | 6/1970 | Matson | 252/316 |
| 3,630,738 | 12/1971 | Dear et al. | 96/82 |
| 4,111,462 | 9/1978 | Lange et al. | 282/27.5 |
| 4,151,201 | 4/1979 | Casnati et al. | 260/562 |
| 4,334,015 | 6/1982 | Yarian | 435/1 |
| 5,041,654 | 8/1991 | Olson et al. | 564/77 |

OTHER PUBLICATIONS

Ephraim, *J. Chem. Ber.* 1891, 24, 1027.
Thomas, D. A., *J. Hetercycl. Chem.*, 1970, 7, 457.
Johnson, J. R. and Ketcham, R. J., *Amer. Chem. Soc.*, 1960, 82, 2719.
Chem Abstracts vol. 72, 1970, 122425n.
Chem Abstracts vol. 71, 1969, 71245k.

*Primary Examiner*—Pamela R. Schwartz
*Attorney, Agent, or Firm*—Gary L. Griswold; Walter N. Kirn; Mark A. Litman

[57] ABSTRACT

This invention relates to improved imaging systems based on the formation of green-yellow colored coordination compounds of transition metals with certain ligands. The formation of colored coordination compounds can be employed to generate images and is important in the manufacture and use of pressure sensitive transfer papers for preparing carbonless copies. In particular, this invention relates to certain 2,5-bis(substituted aryl)thiazolo[5,4-d]thiazole compounds, and particularly to certain 2,5-bis(o-hydroxyaryl)-thiazolo[5,4-d]thiazole compounds, to their coordination compounds with certain transition metals, and to their use in pressure sensitive carbonless copy paper systems. These compounds have been found to provide excellent green-yellow colors when used in pressure sensitive carbonless copy-papers wherein the image is formed by the reaction of a color-forming compound with transition metal salts such as those of nickel, cobalt, iron, copper, and similar materials. These green-yellow color-formers have the advantage of greater solubility in encapsulation solvents and lower volatility than previously used yellow color-formers.

The invention also concerns the admixture of these certain color-formers with N-(monosubstituted)dithiooxamides and/or N,N'-(disubstituted)dithiooxamides to form images of various colors and preferably black images during the application of appropriate pressure to pressure sensitive imaging constructions such as carbonless paper constructions.

24 Claims, 1 Drawing Sheet

THIAZOLO[5,4-D]THIAZOLE COLOR-FORMERS

BACKGROUND OF THE INVENTION

1. Field of Invention

This invention relates to 2,5-bis(substituted aryl)-thiazolo[5,4-d]thiazole compounds, and particularly to 2,5-bis(o-hydroxyaryl)thiazolo[5,4-d]thiazole color-formers, to their reactions with metal salts to form colored coordination compounds, and to imaging systems based thereon. The formation of colored coordination compounds can be employed to generate images and is important in the manufacture and use of pressure-sensitive transfer papers for preparing carbonless copies.

The invention also concerns the admixture of these color-formers with N-(monosubstituted)dithiooxamides and/or N,N'-(disubstituted)dithiooxamides to form images of various colors and preferably black images during the application of appropriate pressure to pressure-sensitive imaging constructions such as carbonless paper constructions.

BACKGROUND OF THE ART

The use of coordination compounds to form imaging sheets has been important in the field of pressure sensitive transfer papers useful for preparing carbonless copies. The present invention provides color-forming compositions which, when complexed with transition metal ions, can provide compositions that exhibit light absorption characteristics such that they appear as intensely green-yellow colored complexes. This is accomplished in the present invention by the use of certain colorless 2,5-bis(substituted aryl)thiazolo[5,4-d]thiazole compounds, and particularly to certain 2,5-bis(o-hydroxyaryl)thiazolo[5,4-d]thiazole compounds which provide an intense green-yellow color when individually complexed with cations of certain transition metals as, for example, nickel$^{2+}$.

An early preparation of a thiazolo[5,4-d]thiazole was reported by Ephraim (see Ephraim, J. *Chem. Ber.* 1891, 24, 1027) in which benzaldehyde was reacted with dithiooxamide to obtain a crystalline product in 25% yield. Later, Johnson and Ketcham identified the product as 2,5-diphenylthiazolo[5,4-d]thiazole (see Johnson, J. R. and Ketcham, R. *J. Amer. Chem. Soc.* 1960, 82, 2719). These workers also prepared a number of other derivatives using substituted benzaldehydes such as o-, m-, and p-hydroxy benzaldehyde, o- and p-methoxy benzaldehyde, furfuraldehyde and cinnamaldehyde. Additional substituted benzaldehydes were also used. These workers also prepared unsymmetrical 2,5-bis(aryl)-thiazolo[5,4-d]thiazoles in which one of the aryl rings contained an o-hydroxy group and the other contained an o-ethoxy group.

The ultraviolet and fluorescent spectra of several thiazolo[5,4-d]thiazole derivatives including those from furfural and cinnamaldehyde have been studied (see Thomas, D. A. *J. Hetercycl. Chem.* 1970, 7, 457).

Sonnenfeld reacted dithiooxamide with a terephthaldehyde to give a reddish-brown self-extinguishing polymer with very good high temperature properties (see Sonnenfeld, R. J. U.S. Pat. No. 3,457,231).

Sawdey describes the use of 2,5-bis(substituted aryl)-thiazolo[5,4-d]thiazole compounds in photographic elements as uv light absorbers (see Sawdey, G. W. U.S. Pat. No. 3,250,617.

Dear and coworkers taught the use of 2,5-bis(substituted aryl)thiazolo[5,4-d]thiazole compounds as both UV absorbers and fluorescent brighteners of both polymers and photographic elements (see Dear, K. M., et al. U.S. Pat. No. 3,630,738).

Dressler and coworkers dyed polypropylene yellow by treating polypropylene containing nickel with 2,5-bis(o-hydroxyphenyl)thiazolo[5,4-d]thiazole. The yellow color resulted from the formation of a nickel/2,5-bis(o-hydroxyphenyl)thiazolo[5,4-d]thiazole coordination compound (see Dressler, H. et al. U.S. Pat. No. 3,326,627).

In none of the above cited literature have 2,5-bis(substituted aryl)thiazolo[5,4-d]thiazole compounds been employed as color-forming ligands to form coordination compounds that provide the basis for an image forming process. That these color-formers can be encapsulated and can be used to form images in pressure sensitive carbonless imaging systems and particularly in combination with other ligands to form various colors in an imagewise fashion also appears new.

Carbonless impact marking papers for the transfer of images, (i.e., carbonless copy papers) are papers which are capable of producing an image upon application of pressure. Products employing this chemistry, generally comprise at least two substrates (for example two sheets of paper) and involve coating one reactant, known as a color-former, on one substrate, and the other reactant, known as a developer, on another, mating, substrate. One surface, or side, of each substrate is coated with one of the two primary reactants. The two substrates are often referred to as a donor sheet and a receptor sheet. Means for preventing the reaction of the two until intended, i.e., until activating pressure is applied, are also provided. This is typically accomplished by encapsulation of one of the reactants. Preferably, a fill solution of the color-forming compound(s) in a hydrophobic solvent are encapsulated or contained in microcapsules and is coated on the back side of one sheet of paper to form a donor sheet. This is then mated with a receptor sheet coated with a developer or reactant for the color-forming compound. The microcapsules serve the purpose of isolating the reactants from one another and preventing reaction. Once activating pressure is applied to the untreated surface of the donor sheet, as from a stylus or business-machine key, the two substrates come into contact under sufficient pressure so that the capsules are rupture in a pattern corresponding to the pattern of applied pressure, and the solution of encapsulated color-former is released and transferred from the donor sheet to the receptor sheet. On the receptor sheet, a reaction between the previously separated reactants occurs. Since the color-former and the developer form a deeply colored image when reacted, an image forms on the receptor sheet. In general, the resulting reaction will form a colored image corresponding to the path traveled by the stylus, or the pattern of pressure provided by the stylus or key. Herein the term, "activating pressure" includes, but is not limited to, pressure applied by hand with a stylus or pressure applied by a business machine key, for example a typewriter key; and the term "encapsulation" and "encapsulated compounds" refer to microcapsules enclosing a fill material therewithin.

A preferred construction comprises an encapsulated color-former dissolved in appropriate hydrophobic solvent(s) within microcapsules and coated onto a back side of the donor sheet with a suitable binder. The back side of the donor sheet is sometimes referred to herein as a "coated back" (CB) sheet. A developer, also optionally in a suitable binder, is coated onto the front side of the receptor sheet herein sometimes referred to as a "coated front" (CF) sheet. Herein, the term "suitable binder" refers to a material, such as starch or latex, that allows for dispersion of the reactants in a coating on a substrate, and is readily rupturable under hand-held stylus pressure, or typical business machine key pressure. As stated previously, in imaging, the two sheets are positioned such that the back side of the donor sheet faces the developer coating on the front side of the receptor sheet. In many applications the uncoated surface of the donor (CB) sheet comprises a form of some type and the activating pressure is generated by means of a pen or other writing instrument used in filling out the form. Thus, the image appearing on the receptor (CF) sheet is a copy of the image applied to the top sheet.

Constructions comprising a first substrate surface, on which is coated the encapsulated color-former; and, a second substrate surface, on which is coated a developer; are often prepared. The coated first substrate surface is positioned within the construction in contact with the coated second substrate surfaces. Such a construction is known as a "set" or a "form-set" construction.

Substrates, with one surface on which is coated the encapsulated color-former, and a second, opposite, surface on which is coated a developer can be placed between the CF and CB sheets, in a construction involving a plurality of substrates. Such sheets are generally referred to herein as "CFB" sheets (i.e., coated front and back sheets). Of course, each side including color-former thereon should be placed in juxtaposition with a sheet having developer thereon. CFB sheets are also typically used in form-sets. In some applications, multiple CFB sheets have been used in form-sets. These contain several intermediate sheets, each having a developer coating on one side and a coating with capsules of color-former on the opposite side.

An alternative to the use of CB, CF, and CFB sheet is the self-contained (SC), or autogenous, carbonless paper in which both the color-former and developer applied to the same side of the sheet and/or are incorporated into the fiber lattice of the paper sheet.

There are many stringent requirements for a color-former. In order to be useful in one embodiment of an imaging construction, it is necessary that the color-former be capable of being encapsulated. In addition, the color-former must be soluble and non-reactive with the fill solvent used for the encapsulation, insoluble in the aqueous solution used as the dispersing phase, non-reactive with other color-formers present in the encapsulation medium, and non-reactive with the materials used to form capsule walls.

It is also desirable that the color-former be capable of rapidly forming a stable colored image upon contact with a developer on a receptor sheet. That is, the color should form nearly instantaneously, so that the image is rapidly formed as the stylus pressure is applied to the backside of the donor sheet. This will help ensure formation of an accurate, almost instantly readable copy. The image should also be relatively stable so that it does not substantially fade with time.

One type of carbonless imaging chemistry takes advantage of the fact that dithiooxamide compounds are encapsulable and react readily with many transition metal salts to form coordination complexes. The chemistry and characteristics of certain dithiooxamide materials have been used successfully as color-formers in commercially available carbonless paper products. Generally, these dithiooxamide compounds comprise symmetrically disubstituted dithiooxamide compounds and include N,N'-dibenzyldithiooxamide and N,N'-di(2-octanoyloxyethyl)dithiooxamide.

Transition metal salts used as developers to form coordination complexes with dithiooxamides which have been employed in the preparation of carbonless image transfer products or constructions are generally those comprising cations having a +2 valance state. Compounds with nickel, zinc, palladium, platinum, copper and cobalt all form such complexes with dithiooxamides. Many of these coordination complexes are deeply colored.

Due to the stoichiometry of the system (i.e., the metal salt is usually in excess since relatively little ligand is released), it is generally believed that the image formed on the receptor sheet after stylus pressure is applied to break the capsules and release the ligand, results from the formation of a complex between one molecule of color-forming ligand and 1 or 2 atoms of a metal having a +2 valence (as for example $Ni^{2+}$). The counterion of the positively charged transition metal is usually the conjugate base of a weak acid and may facilitate removal of the two protons from the color-forming ligands, necessary for complexation with the $M^{2+}$ cation.

In commercial applications nickel salts have been preferred as the transition metal salts. One reason for this is that nickel salts form a deep color when complexed with dithiooxamide ligands. The nickel salts are also substantially colorless, and thus do not alone impart color to the receptor (CF) sheet. A third reason is that nickel salts are relatively low in cost, in comparison to other transition metal salts that can be easily and safely handled and that form highly colored coordination complexes with dithiooxamides.

In some applications it is also desirable that the color of the complex be a deep, strong color that is not only pleasing to the eye, but that will exhibit good contrast with the paper, for purposes of later reading and/or photocopying. This has been one drawback with conventional carbonless paper arrangements, which use nickel salts complexed with disubstituted dithiooxamide ligands. The image imparted by the resulting coordination compound, under such circumstances, is generally referred to as blue/purple (b/p) or magenta. The more "red" character the coordination complex exhibits, generally the less contrasting and pleasing is the appearance. A dark, i.e., preferably black, blue, or blue-black, arrangement would be preferred.

One attempt to prepare a neutral black image using metal coordination chemistry of this type was provided by Yarian (see Yarian, D. R. U.S. Pat. No. 4,334,015). He found that the combination of certain aromatic-substituted hydrazones with dithiooxamides followed by encapsulation of the mixture provides a method of achieving a dark image. These hydrazones react with the metal on the receiving sheet to form intense green-yellow images. The green-yellow coordination compound thus formed, combined with the blue-purple image formed by the dithiooxamide (such as N,N'-di(2-octanoyloxyethyl)dithiooxamide and/or N,N'-(dibenzyl)dithiooxamide), results in an image that appears almost black to the observer.

Although this is a successful approach, Yarian's use of hydrazones still suffers from several drawbacks. The solubility of the hydrazones is not as great in the solvents generally used in the encapsulation process as are dithiooxamides. In addition, the initial image color of the coordination compound formed with N,N'-(disubstituted)dithiooxamides is brown and only after some time does the blue-black to black final image color form. Although much better than the blue-purple coordination compound formed with N,N'-(disubstituted)dithiooxamides, this mixture of green-yellow and blue-purple is a dark blue-black rather than the preferred neutral black.

Yarian also noted that the color of capsules prepared from hydrazone compounds was pH dependent and their color may change from essentially colorless at low pH to yellow at pH greater than 9.5 to 10. Yarian further noted that this color change is rapid and reversible upon lowering of the pH. Papers can be divided into classes depending upon their methods of manufacture, treatment and sizing. Among these classifications are acidic and alkaline papers. Encapsulated hydrazones when coated onto "alkaline paper" can form yellow colors.

In conventional impact imaging constructions, the capsules can be inadvertently ruptured in steps such as processing, printing, cutting, packaging, handling, storing, and copying. In these situations inadvertent marking or discoloration (i.e., backgrounding) of the sheets results from inadvertent capsule rupture and transfer of the encapsulated material to the mating sheet where color formation occurs. The amount of inadvertent backgrounding has been reduced in such products by the use of a color control coreactant distributed externally among the capsules. This coreactant is capable of reacting with the contents of the ruptured capsules before transfer of said contents to the receptor sheet and formation of an undesired image (see Ostlie, D. A., U.S. Pat. No. 3,481,759). Ostlie discovered that addition of a small amount of a metal salt such as a zinc salt to the capsule coating prevents the formation of colored background. The zinc metal ion reacts with the accidently released dithiooxamide compound to form colorless coordination compounds and thus deactivates inadvertantly released dithiooxamide materials.

The use of Yarian's invention in combination with that of Ostlie is not possible as zinc forms yellow coordination complexes with the hydrazones of Yarian's invention. Thus, yellow color backgrounding still occurs on the backside of the sheet due to inadvertently ruptured capsules. It would be desirable to have a yellow color-former that could be successfully deactivated by the same method as that described by Ostlie's discovery. Then, the same method of deactivation of the yellow, magenta, and cyan color-formers released by inadvertent capsule rupture would be possible.

Another approach to formation of a black image employs an encapsulated mixture of an acid sensitive green-forming leuco dye and a dithiooxamide color-former. The receptor sheet is formulated to contain phenolic type acids in addition to the transition metal salts. In this system, pressure imaging results in the release of both acid sensitive leuco dyes and dithiooxamide materials. The nickel salt in the receptor sheet reacts with the dithiooxamide to form a purple color and the phenolic acid in the receptor sheet reacts with the acid-sensitive leuco to form a green color. Together they generate a black image. This approach, while successful, has several disadvantages. Heavy coatings to the papers are required as two separate chemistries are involved. Another drawback of this approach is that the rates of reaction for the two chemistries are different and must be balanced by adjustment of the ratios of the two chemistries in the paper construction.

Recently, a blue or blue-black image was achieved by employing encapsulated N-(monosubstituted)dithiooxamides compatible with the transition metal chemistry described above (see copending U.S. patent application Ser. No. 07/483,776 incorporated herein by reference). Preparation of these N-(monosubstituted)dithiooxamides is described in Olson, D. B., et al. U.S. Pat. No. 5,041,654 which is incorporated herein by reference for the disclosure and synthesis of these N-(monosubstituted)dithiooxamides. These may be used either alone or in admixture with N,N'-(disubstituted)dithiooxamides and can result in a cyan, blue, or blue-black image. A neutral black image would be preferred.

The ligands generally useful in carbonless paper constructions should also be relatively nonvolatile, so that free ligand, which would result from any inadvertently ruptured capsule, does not readily transfer from the donor sheet to the receptor sheet and form undesired spots of imaged area. That is, so that without the specific assistance of stylus or key pressure, transfer is not readily obtained.

It is also preferred that the ligands should be colorless, since the ligands are often encapsulated and coated onto the backside of a sheet, such as a form, which has printing on one or both sides thereof. This allows for good legibility of printing on the back side of the carbonless copy-paper sheets. This aspect is particularly important if the donor sheet comprises a top sheet for a stack of carbonless papers. Such sheets are often white, so that they can be readily identified as originals, can be readily photocopied, and can be easily read. The presence of color in the coating on the back side of this sheet would detract from the white colored "original" appearance and could make photocopying of this sheet troublesome.

While the above-described preferred characteristics have long been desirable, they have not been satisfactorily achieved with conventional reactants and conventional constructions. What has been needed has been suitable materials and arrangements for achieving the desired features described.

SUMMARY OF THE INVENTION

It is one aspect of this invention to describe color-forming ligands and compositions useful in encapsulated imaging systems wherein color is formed by formation of a complex between a transition metal cation and a green-yellow color-former. This is accomplished in the present invention by the use of certain 2,5-bis(substituted aryl)thiazolo[5,4-d]thiazole compounds and most preferably to certain 2,5-bis(o-hydroxyaryl)-thiazolo[5,4-d]thiazole compounds which provide a green-yellow color when individually complexed with nickel$^{2+}$.

The central nucleus of 2,5-bis(substituted aryl)-thiazolo[5,4-d]thiazole color-forming compounds which are useful in the present invention and are capable of forming colored complexes with transition metal salts can be represented by the following formula, I, as follows:

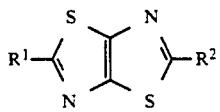

wherein R¹ is selected from the group of substituents comprising an ortho-hydroxy substituted aryl group and R² is a substituent independently selected from the group of substituents consisting of an aryl group or hydrogen.

When the term "group" is used to describe a chemical compound or substituent, the described chemical material includes the basic group and that group with conventional substitution. Where the term "moiety" is used to describe a chemical compound or substituent only an unsubstituted chemical material is intended to be included. For example, "aryl group" includes not only such aryl moieties as phenyl, naphthyl, furyl, thienyl, etc., but also such moieties bearing substituent groups such as halogen, cyano, hydroxyl, nitro, amino, carboxylate, etc., and on alkyl groups, internal substitution such as ether oxygen atoms. On the other hand, "aryl moiety" includes only unsubstituted phenyl, naphthyl, furyl, thienyl, etc.

The invention also includes within its scope, new 2,5-bis(o-hydroxyaryl)thiazolo[5,4-d]thiazole compounds and derivatives of these compounds whereby alkyl groups are substituted on the o-hydroxysubstituted aromatic rings. These new compounds are soluble in solvents favored in the encapsulation processes employed in carbonless imaging constructions and the preferred compounds are also low in volatility. When these thiazolo[5,4-d]thiazoles react with certain metal salts, and especially with nickel salts, strongly green-yellow colored coordination complexes are formed. The invention also includes within its scope new coordination complexes of bis-2,5-(o-hydroxyaryl)-thiazolo[5,4-d]thiazole compounds with various transition metals such as $Ni^{2+}$.

The ligands of the present invention are derivatives of the parent thiazolo[5,4-d]thiazole ring system. The Chemical Abstracts Registry Number for this compound is [251-56-59]. These compounds are formed by the reaction of dithiooxamide (rubeanic acid) with an aromatic aldehyde. For example, reaction of 2 molecules of benzaldehyde with one molecule of dithiooxamide affords 2,5-diphenylthiazolo[5,4-d]thiazole. The Chemical Abstracts Registry number for this compound is [6641-96-9]. Similarly, the compound derived from the reaction between o-hydroxybenzaldehyde (salicylaldehyde) and dithiooxamide is 2,5-bis(o-hydroxyphenyl)thiazolo[5,4-d]thiazole. The Chemical Abstracts Registry number for this compound is [10398-63-7]. Compounds derived from the condensation of aromatic aldehydes with dithiooxamide are herein referred to as 2,5-bis(substituted aryl)-thiazolo[5,4-d]thiazole compounds.

It is another aspect of this invention to teach the preparation of colored coordination compounds of transition metals with the ligands comprised of these 2,5-bis(substituted aryl)thiazolo[5,4-d]thiazole compounds.

It is also an aspect of this invention to described green-yellow color-formers useful as imaging compositions wherein a mixture of color-formers and the color is formed by the formation of a complex between a transition metal cation and the mixture of color-formers.

It is a further aspect of this invention to demonstrate that green-yellow color-forming compounds of the type described above can be encapsulated and utilized to form carbonless copy papers that provide strong green-yellow images. When a mixture of color-formers is encapsulated, images of varying colors can be formed by the formation of a complex between a transition metal cation and the encapsulated color-formers. In particular, when mixed with cyan and magenta color-formers, or mixtures thereof, black images can be formed.

The invention further includes within its scope the provision of a carbonless copy paper system or construction utilizing material according to formula I above, as a reactant. In a preferred embodiment, the construction comprises: a donor sheet having encapsulated color-forming ligand according to formula I thereon; and, a receptor sheet having a coating of transition metal salt, preferably a $Ni^{2+}$ salt, thereon. The encapsulation provides means inhibiting reaction between the ligand and the transition metal cation, until appropriate activating pressure is applied to the arrangement.

It will also be understood that in some instances a black color could also be formed by the mixing of the green-yellow color-former with magenta or blue/purple color-formers.

The invention also includes within its scope a method of forming an image on a receptor sheet comprising: providing a receptor sheet having a surface with a transition metal salt coated thereon; and, transferring to the coated surface of the receptor sheet an effective amount of a compound of structure I. The compound can be volatile or nonvolatile; however, in preferred applications, it will be a nonvolatile compound according to formula I.

DETAILED DESCRIPTION OF THE INVENTION

The Green-Yellow Color former

Figure 1:
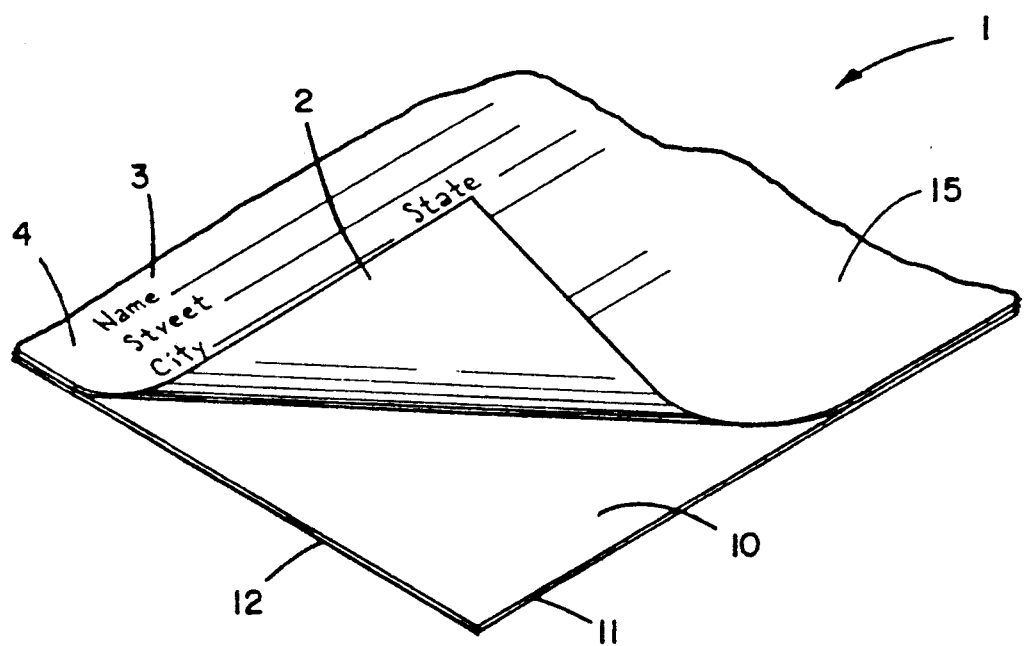
FIG. 1 is a fragmentary perspective view of a carbonless paper construction according to the present invention, depicted with the first and second substrates thereof partially separated.

We have found that certain 2,5-bis(substituted aryl)-thiazolo[5,4-d]thiazole compounds form green-yellow coordination compounds with nickel salts, such as nickel 2-ethylhexanoate, nickel rosinate, nickel stearate, nickel benzoate, nickel oleate, nickel hydrocinnamate, nickel 2-phenylbutyrate, nickel calcium rosinate and the like. The formation of coordination compounds can provide the basis of a pressure sensitive or thermographic imaging system.

In order to be useful in an encapsulated imaging system, the color-forming ligand must satisfy several requirements. It must be encapsulable and therefore not be highly soluble in water. The color-former should also be stable over the wide pH conditions encountered during a typical encapsulation process and it should have sufficiently low volatility so that the free ligand resulting from inadvertently ruptured capsules does not transfer from the CB to the adjacent CF sheet and form spots of imaged area. It should have low coloration in the uncomplexed state and form a stable colored image upon contact with the metal from the CF sheet.

For the formation of a carbonless paper construction, the encapsulation process requires the color-forming ligand be dissolved in a solvent or mixed solvents. Thus, the preferred 2,5-bis(o-hydroxyaryl)thiazolo[5,4-d]thiazole compounds must be soluble in a solvent used in the encapsulation process. Such aqueous immiscible solvents include xylene, toluene, cyclohexane, diethyl phthalate, tributyl phosphate, benzyl benzoate, diethyl adipate, butyl diglyme, and the like.

The solubility of these, 2,5-bis(o-hydroxyaryl)-thiazolo[5,4-d]thiazole green-yellow color-former compounds (i.e., 2,5-bis(o-salicylidene)thiazolo[5,4-d]thiazole compounds), exemplified by structure I in nonaqueous solvents such as those used in the encapsulation process may be increased by substituting alkyl, alkoxy, alkenyl, or such groups for the hydrogens on the various positions available in groups $R^1$ and $R^2$ of the structure I above. This increase in solubility occurs without reduction in imaging speed. Thus, the condensation of dithiooxamide with 3,5-di-t-butylsalicylaldehyde to form 2,5-bis(3,5-di-t-butylsalicylidene)-thiazolo[5,4-d]thiazole compounds (compound 2 below) results in a compound that is very soluble in encapsulation solvents. Likewise, the condensation product between dithiooxamide and 2-hydroxy-3-methoxybenzaldehyde (o-vanillin) also results in a ligand (compound 6 below) with good solubility in capsule solvents. Preferred substituents on the aromatic ring contain alkyl groups, alkoxy groups, alkenyl groups of from 1-10 carbon atoms substituted on the ring, and a hydroxyl group ortho to the aldehyde or ketone. Several of the preferred compounds of this invention are themselves new compounds, never having been described before. Representative compounds of structure I are shown in Table 1 below.

Representative compounds of the invention satisfy the requirements of solubility in suitable solvents for encapsulation, non-solubility in aqueous media, non-reactivity with fill solvents and color-formers mixed therewith, compatibility with existing transition metal/-dithiooxamide imaging systems, and low volatility at room temperature, i.e., about 25° C. In addition, they are generally colorless to lightly colored color-formers, and impart little or no color to the sheets upon which they are coated in use. Finally, they form generally green-yellow colors on coordination with at least some transition metal ions, such as nickel.

The most preferred compounds satisfy all the above requirements, plus they are generally nonvolatile at elevated temperatures, i.e., above about 25° C., most preferably above about 49° C. The most preferred compounds include: 2,5-bis-(o-hydroxyaryl)thiazolo[5,4-d]thiazole compounds as for example 2,5-bis(o-hydroxyphenyl)thiazolo[5,4-d]thiazole and substituted versions thereof. That these materials are the most preferred will be apparent from the experiments as reported herein below.

It will be understood that in some instances the encapsulated color-formers may comprise, in addition to the green-yellow color-former of formula I, a mixture of an N-(monosubstituted)dithiooxamide (capable of forming blue or cyan image on coordination) and an N,N'-(disubstituted)dithiooxamide (capable of forming magenta or purple color). Should this latter be the case, a generally dark overall color would result upon image formation, provided, however, that an effective amount (i.e., an amount effective to produce a dark black image rather than a green-yellow image) of dithiooxamide color-formers were also present.

It will also be understood that in some instances the carbonless copy paper system may comprise a mixture of capsules, each containing separate encapsulated color-forming ligand solution. In this instance, color would be formed by the mixing of the color-formers upon capsule rupture and reaction with the metal cation. Again, the use of a mixture of capsules each individually containing green-yellow, magenta or cyan color-former would result in a black color upon image formation, provided, however, that an effective amount (i.e., an amount effective to produce a dark black image rather than a green-yellow image) of dithiooxamide color-formers were also present.

Aromatic aldehydes that do not contain a hydroxy group ortho to the point of attachment of the aromatic ring to the thiazolo[5,4-d]thiazole nucleus also condense with dithiooxamide to form soluble products. However, their coordination product with nickel is weakly colored and is less suitable for imaging chemistry. Thus, at least one of $R^1$ or $R^2$ must contain a group capable of coordination with a transition metal, ortho to the site of attachment of the aromatic ring to the thiazolo[5,4-d]thiazole nucleus.

A further consideration to the commercial exploitation of the invention is the ease of preparation of the compounds exemplified by structure I. 2,5-bis(substituted aryl)thiazolo[5,4-d]thiazole compounds and related compounds according to the general formula I can be readily prepared through synthetic methods known in the literature and further described herein, by the reaction of an aromatic aldehyde with dithiooxamide. The reaction proceeds readily at reflux using excess aldehyde or dimethylformamide as solvent and the product separates as a pale yellow solid.

Aminoplast condensations of urea or melamine with an aldehyde such as formaldehyde or mixtures of aldehydes to form the capsule shell is carried out in an acidic aqueous medium. Other microcapsule shell formation reactions occur in highly basic media. Compounds according to formula I as defined are generally insoluble in aqueous solution, soluble in the aqueous-immiscible solvents favored as capsule fill solvents, and stable over a pH range of about 1 to 9, and thus are readily encapsulatable. Compounds included within the scope of formula I as defined also generally readily form green-yellow images upon coordination with at least certain transition metal salts, and most preferably nickel salts.

The preferred 2,5-bis(o-hydroxyaryl)thiazolo[5,4-d]thiazole color-formers of the present invention are more soluble in the solvents generally used in the encapsulation process and are also less sensitive to color change upon adjustment of pH and maintain their essentially colorless nature when encapsulated and coated onto "alkaline paper."

It is also a feature of the present invention that the liquid employed as the solvent for the encapsulated reactant can be a solvent for the coreactant (such as the metal salt) as well, whether the latter is also encapsulated or not. This same solvent then serves as a reaction implementing medium for the two reactants at the time of rupture of the capsules and is commonly referred to as a cosolvent. Examples of cosolvents which fulfill the above mentioned criteria are cyclohexane, tributyl phosphate, diethyl phthalate, toluene, xylenes, 3-heptanone, benzyl benzoate, diethyl adipate, butyl diglyme, and the like. The selection of additional suitable cosolvents will be obvious to those skilled in the art.

It is another feature of this invention that the green-yellow color-formers are compatible with metal/dithiooxamide imaging chemistry. They are soluble in the same encapsulation solvents as the dithiooxamides. They also do not react with either the dithiooxamides or the encapsulation solvent. This allows one "imaging chemistry" to be used.

Those compounds that are relatively nonvolatile at temperatures of at least about 49° C., and preferably up to at least about 71° C., are particularly useful in the embodiments of the invention. Again, the term "nonvolatile", when used with respect to the color-formers according to the present invention, is meant to refer to compounds that pass the volatility test outlined herein below. That is, the compounds are classifiable as nonvolatile under the conditions of the test.

The color-forming compositions of the present invention can be readily microencapsulated by techniques known in the art (see for example Matson, G. W. U.S. Pat. No. 3,516,941. Pressure-sensitive record and/or transfer sheets can be provided as are known in the art.

Then compared with the green-yellow color-formers described by Yarian, vide supra, the green-yellow color-formers of the present invention, represented by structure I, form relatively colorless complexes with $Zn^{2+}$ salts. Thus, the use of the color-formers of the present invention in combination with the color control coreactants taught by Ostlie is now possible and the same method of deactivation of the color-formers released by inadvertent capsule rupture can now be used.

The Metal Complex

In a typical application, to generate an image on a substrate, the complex is formed by contacting the color-former (or a solution containing the color-former) with a substrate having a coating of transition metal salt thereon. The preferred transition metal salts are those of nickel; however, salts of copper, iron, and other transition metals may, in certain applications, be used within the scope of this invention. Examples of transition metal salts for this application are nickel 2-ethylhexanoate, nickel rosinate, nickel stearate, nickel benzoate, nickel 2-phenylbutyrate, nickel oleate, nickel hydro-cinnamate, nickel calcium rosinate, and the like (see Lange, H. E. U.S. Pat. No. 4,111,462). Preferred transition metal salts for use in this invention are nickel rosinate, nickel 2-hexanoate, and mixtures thereof. Again, formation of the complex is evidenced by appearance of a strong green-yellow color shortly after the imaging impact takes place.

Although the exact nature of the metal complex between the 2,5-bis(substituted aryl)thiazolo[5,4-d]thiazole compounds and the transition metal is not known, it is believed that the preferred 2,5-bis(o-hydroxyaryl)thiazolo[5,4-d]thiazole compounds of the present invention have two separate coordination sites and thus can coordinate with one or two transition metal ions having a +2 charge. As the preferred transition metal ion, $nickel^{2+}$, prefers to be tetracoordinate, the two remaining coordination sites of each $Ni^{2+}$ atom may be occupied by a coordination site of another 2,5-bis(o-hydroxyaryl)thiazolo[5,4-d]thiazole molecule used in the color-forming reaction process. An example of one possible structure for the coordination complex between $Ni^{2+}$ and 2,5-bis(o-hydroxyphenyl)-thiazolo[5,4-d]thiazole is shown is structure II below. It will be understood to those skilled in the art that II represents but one isomer of several that are possible.

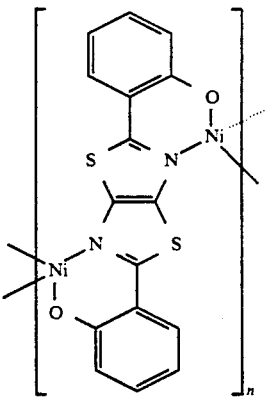

When the 2,5-bis(o-hydroxyaryl)thiazolo]5,4-d]thiazole compounds of this invention are mixed with N,N'-(disubstituted)dithiooxamide color-formers which form a magenta image, or N-(monosubstituted)dithiooxamide color-formers which form a cyan image, or a mixture of the two which form a blue image, a polymeric coordination compound may result containing mixtures of these compounds.

The structure of the aldehyde is also relevant to the present invention. When aromatic aldehydes are employed in the condensation reaction with dithiooxamide it is preferred that there should be an electron donating group ortho to the aldehyde group. This provides an additional coordination site for the metal in addition to the nitrogens or sulfur of the thiazolo[5,4-d]thiazole portion of the molecule and enhances the color. Suitable groups include hydroxyl, and thiol. Hydroxyl groups are preferred. The compounds in Table 2 demonstrate the need for a group capable of strong coordination with a transition metal in the ortho to the site of attachment of the aryl group to the thiazolo[5,4-d]thiazole ring nucleus. This is evidenced by compound 3, prepared from benzaldehyde and compound 5, prepared from 2-methoxybenzaldehyde. When complexed with nickel the coordination compound formed is very weakly yellow and the measured reflectance density and Chroma are low. In compound 8, the group capable of coordination with the transition metal is para to the site of attachment of the aryl group to the thiazolo[5,4-d]thiazole ring nucleus and the color formed with the transition metal is very weak (lower Chroma). This is thought to be due to the inability of the transition metal to coordinate with the nitrogens or sulfur of the thiazolo[5,4-d]thiazole portion molecule along with the electron donating group in the para-position of the aromatic group. Aliphatic aldehydes also condense with dithiooxamide but these materials do not ring close to form 2,5-dialkylthiazolo[5,4-d]thiazoles. The condensation products of heterocyclic aromatic aldehydes and ketones afford ligands of structure I capable of additional coordination through the heteroatom in a pseudo-ortho position. This is exemplified by compound 4, prepared from furfuraldehyde, in Table 2. The chroma of this compound is also low and further demonstrates the need for a group capable of strong coordination with the transition metal.

Compounds containing only one o-hydroxyaryl group on the thiazolo[5,4-d]thiazole nucleus would also be expected to form colored complexes with transition metals such as nickel$^{2+}$.

The colors of various other 2,5-bis(substituted aryl)-thiazolo[5,4-d]thiazole compounds are shown in Table 2. As noted above, the most preferred ligands are those that provide a strong green-yellow color upon coordination with nickel$^{2+}$ and are also soluble in the solvents useful for encapsulation.

As shown in Experimental Examples 5 and 6 and Tables 3 and 4 below, when the green-yellow color-formers of the present invention are used in admixture with certain conventional dithiooxamide derivative transition metal complexing compounds, the light absorption properties of the individual complexes are additive. It is possible to absorb such a substantial portion of light in the visible spectrum so as to providing a neutral, black color. By proper combination of materials additional colors can be formed. For example a mixture of the green-yellow color-former of this invention with a cyan color-former such as an N-(monosubstituted)dithiooxamide will afford a green image. When a green-yellow color-former of this invention is mixed with an effective amount of an N-(monosubstituted)dithiooxamide which provides a cyan image and an N,N'-(disubstituted)dithiooxamide which provides a magenta image; or mixtures thereof which provide a dark blue to blue-black image, the resulting complex composition appears almost black to the observer.

As demonstrated in Table 2, the colors of the 2,5-bis-(o-hydroxyaryl)thiazolo[5,4-d]thiazoles have a green component and are best referred to as green-yellows. For example, compounds 1, 2, 6, and 7 are green-yellow compounds. Because of their green component a neutral black image can be now be obtained by the use of N,N'-(disubstituted)dithiooxamide or mixtures of N,N'-(disubstituted)dithiooxamide magenta color-formers and the addition of a N-(monosubstituted)dithiooxamide cyan color-former is not necessary. This is shown in Tables 3 and 4 below. This is advantageous as it only requires the preparation of two classes of compounds (green-yellow and magenta) rather than three (yellow, magenta, and cyan). In addition, the preparation of N-(monosubstituted)dithiooxamides is still not as facile as that of N,N'-(disubstituted)dithiooxamides.

It is noted that complexes formed with the green-yellow color-formers of the present invention are relatively stable. Further, even if some reversal of coordination does occur, the relatively nonvolatile 2,5-disubstituted-thiazolo[5,4-d]thiazole compounds of this invention will remain on the surface of the receptor sheets, and thus recoordinate.

Carbonless Imaging Constructions

The invention further includes within its scope image transfer systems or constructions, i.e., carbonless impact marking papers for the transfer of images. In general, this involves coating one reactant, the color-former on one substrate, and the transition metal salt (the other reactant) on another, mating, substrate. Means for preventing reaction of the two until intended, i.e., until activating pressure is applied, are also provided. Preferably, the color-forming compounds are contained or encapsulated in microcapsules on one sheet of paper. The reactant for the color-forming compound, i.e., the transition metal salt, is carried on a mating sheet of paper. The microcapsules serve the purpose of isolating the reactants from one another (i.e., preventing reaction) until such time as pressure is applied to the paper for the purpose of creating an image.

Generally, a carbonless paper construction comprises at least two substrates, for example two sheets of paper, each with one surface, or side, coated with one of the two primary reactants. The two substrates are generally referred to as a donor sheet and a receptor sheet. When the coated faces, or surfaces, of the two substrates come into contact under sufficient pressure so that the reactants can mix, a reaction occurs and an image forms on the receptor sheet.

A preferred construction 1 (FIG. 1) comprises the encapsulated color-forming ligands dissolved in an appropriate solvent(s) within microcapsules (not shown) and coated onto a back side 2 of a donor sheet 3 in a suitable binder. The back side 2 of donor sheet 3 is sometimes referred to herein as a coated back (CB) sheet 4. The metal salt, preferably a Ni$^{2+}$ salt, optionally in a suitable binder, is coated onto a front side 10 of a mating, or receptor, sheet 11, herein sometimes referred to as a coated front (CF) sheet 12. As stated previously, in imaging, the two sheets are positioned such that the back side 2 of donor sheet 3 faces the metal salt coating on the front side 10 of the receptor sheet 11 as shown in FIG. 1. When activating pressure is applied to face 15 of the donor sheet 3, the capsules rupture and release the color-forming ligand for transfer to the receptor sheet 11, forming a colored pattern due to complexing with the salt. It is noted that in FIG. 1 the coated back (CB) sheet 4 and the coated front (CF) sheet 12 are shown partially separated to facilitate understanding of the invention. Herein, "activating pressure" includes, but is not limited to, pressure applied by hand with a stylus or pressure applied by a business machine key, for example a typewriter key.

Also included within the scope of the invention is a construction comprising: a plurality of first substrate surfaces, each on which is coated the encapsulated color-former; and, a plurality of second substrate surfaces, each on which is coated a salt of a transition metal cation with a +2 oxidation state. Each of the coated first substrate surfaces is positioned within the construction in contact with one of the coated second substrate surfaces. Such a construction is known as a form-set construction.

Substrates, with one surface on which is coated the encapsulated color-former, and a second, opposite, surface on which is coated a salt of a transition metal cation (as for example Ni$^{2+}$) can be placed between the CF and CB sheets, in a construction involving a plurality of substrates. Such a sheet is sometimes referred to as a CFB sheet. Of course, each side including color-former thereon should be placed in juxtaposition with a sheet having metal salt thereon. CFB sheets are typically used in form-sets.

The color-forming compounds and compositions of the present invention can be used in the manner that dithiooxamide (DTO) based chemistries have previously been used. Indeed, one advantage of the green-yellow color-formers of the present invention is their ability to image using the same transition metal coordination chemistry employed in dithiooxamide based imaging systems. For example, pressure sensitive carbonless transfer and record sheets which are capable of providing colored images can be provided by encapsulating the green-yellow color-forming compounds of the present invention and a cosolvent vehicle in substantially impermeable, pressure-rupturable microcapsules and applying these encapsulated materials to paper substrates. Alternatively, a composition comprising the green-yellow color-forming compounds of the present invention in a cosolvent vehicle can be carried by a variety of materials such as woven, non-woven or film transfer ribbons for use in impact marking systems such as typewriters and the like, whereby the green-yellow color-former is transferred to a record surface containing a transition metal salt by impact transfer means. Further, a composition comprising the green-yellow color-former and a cosolvent vehicle could be absorbed in a porous pad for subsequent transfer to a coreactive record surface by transfer means such as a portion of the human body, e.g. a finger, palm, foot or toe, for providing fingerprints or the like.

Preparation of Substrate (Donor Sheet) Coated with Encapsulated Green-Yellow Color-former A carbonless copy construction comprises a substrate containing microcapsules filled with a compound of formula I dissolved in a suitable fill solvent or solvents, the solution of which is water-insoluble. Preferably, the shell of the capsules are of a water-insoluble urea-aldehyde, e.g., urea-formaldehyde product formed by acid-catalyzed polymerization of a urea-formaldehyde precondensate (see G. W. Matson, vide supra, incorporated herein by reference).

A capsule slurry, as prepared from a mixture of the urea-formaldehyde precondensate and a fill material containing green-yellow color-formers of structure I, is combined with a binding agent, such as aqueous sodium alginate, starch, latex, or mixtures thereof for coating on one face of a substrate. In the preferred embodiment, the back of the donor sheet is coated with the capsule slurry, and is referred to as the coated back (CB) sheet.

Preparation of Substrate (Receptor Sheet) Coated with Metal Salt

The receptor sheet with the transition metal salt coated thereon (also known as the developer sheet) comprises the transition metal salts of organic or inorganic acids. The preferred transition metal salts are those of nickel, although copper, iron, and other transition metals may be used to advantage in some applications.

Inorganic acids that can be used to react with the transition metals to form the transition metal salts are acids whose anions form salts with transition metals and that will dissociate from the transition metal in the presence of the color-forming ligand for the color-forming reaction. Typical inorganic acids are nitric acid and sulfuric acid, which form nickel nitrate and nickel sulfate, respectively.

Organic acids that are useful in forming the transition metal salts, and that readily dissociate in the presence of color-forming ligands, are the aliphatic and aromatic mono- and di-carboxylic acids, substituted aliphatic and aromatic monocarboxylic acids, and heterocyclic monocarboxylic acids. Monocarboxylic aliphatic acids containing about 6 to 20 carbon atoms are preferred. Nickel 2-ethylhexanoate is a particularly preferred color-forming transition metal salt. Other representative transition metal salts are the nickel, iron, and copper salts of the described organic acids. Examples of such are nickel rosinate, nickel calcium rosinate, nickel stearate, nickel 2-phenylbutyrate, nickel oleate, nickel benzoate, and nickel hydro-cinnamate, as well as the copper and iron analogues. Also, included within the scope of the invention are mixtures of these compounds.

The composition including the transition metal salt may be coated on substrates by conventional coating techniques. The transition metal salt is preferably coated on the front side of a substrate, such as a sheet of paper which is referred to as the coated front (CF) sheet. Additionally, the transition metal salt may be formulated into printing compositions and be printed onto all or a portion of a substrate, such as paper (see, for example, H. E. Lange, vide supra).

Evaluation of Volatility

The preferred compounds of the present invention exhibit a preferred volatility level, and are most favored for use in carbonless imaging transfer systems such as the preferred ones described above, in which selected formation of a green-yellow image is desired. The method utilized in the experiments to both define and evaluate the level of volatility was as follows. A single sheet piece of Grade #10 (20×12 cm) cheesecloth (obtained from American Fiber and Finishing, Inc., Burlington, Mass., AF & F., Item No. 588033), was placed between a simulated donor sheet and a receptor sheet of a carbonless paper construction. The simulated donor sheet comprised a sheet of paper saturated with color-former of structure I, which was used to simulate a CB sheet with ruptured capsules. Pressure was then applied for 24 hours by placing 9 pounds of paper on top of the sheets, to simulate storage conditions of the paper packages. The formation of color on the receptor sheet, due to transfer of volatile color-former thereto, was used as an indication that the particular color-former was less than optimally desirable for carbonless paper constructions, i.e., was volatile. A compound was considered generally to be nonvolatile, within the meaning of the term as used herein to define the present invention and thus to define color-formers most acceptable for use in carbonless image transfer arrangements, if no color was formed after the simulated test was run for about 24 hours at 25° C. In some instances, if no color was formed after storage at room temperature (25° C.), successively higher temperatures were used, as for example 49° C., 60° C., and 71° C. This will be better understood by reference to Experiments 2 and 3 below. In general, the most preferred compounds, with respect to volatility, are those which do not substantially generate color appearance under the conditions of the test, even at the higher temperatures.

Determination of Complex Color

In general, the colors of the complexes, as listed in Experiments 1-6 and in Tables 2-4 below, were determined by preparing a solution of the color-former or mixture of color-formers in an appropriate solvent. Unless otherwise indicated, the solvent was composed of a mixture of tributyl phosphate (26.5%), diethyl phthalate (17.6%), and cyclohexane (55.9%). The images were formed by applying two stripes of the solution to a substrate coated with a $Ni^{2+}$ coated receptor sheet using a cotton tipped applicator swab. Rapid and complete development of the image was achieved by passing the sheet through a hot shoe adjusted to 102° C., making a revolution every 10 seconds. The visually observed colors were measured and recorded.

One method of color measurement is to determine the color's position in color space. One color space system is the Hunter System; see F. W. Billmeyer, Jr., and M. Saltzman, *Principles of Color Technology*; John Wiley & Sons; New York, N.Y.; Ch. 2 and 3, 1981. In this system three mutually perpendicular axes (L, a, and b) are needed to define a color. "L" (+z axis) represents the lightness or darkness of the image; "a" (x axis) represents the amount of red or green (+a is red, −a is green); and "b" (y axis) represents the amount of yellow or blue (+b is yellow, −b is blue). By measuring a material's L, a, and b values, the color of one sample can be compared with that of other samples. Another value used in the Hunter System is Chroma (C). Chroma is defined by the equation $[C=(a^2+b^2)^{\frac{1}{2}}]$ and represents the distance of the image coordinates from the origin. The greater the Chroma, the more intense the image. Chroma is used to compare images of the same hue. Because the color of a sample is also dependent upon the color temperature of the illuminating source, the angle at which the sample is illuminated, the angle at which the illumination is reflected, and the angle of the retina illuminated, these all need to be specified. Many instruments have been developed to record these values. One such instrument is the HunterLab LabScan II. This instrument is capable of automatically determining the L, a, and b values for a given sample, and was used for the following examples.

The L, a, and b color coordinates of the more uniform stripe were measured for 45°/0° reflectance on a HunterLab LabScan II, secondary observer, using illuminant C. The observed (image) color and the Hunter coordinates for $Ni^{2+}$ complexes of the green-yellow color-formers of this invention are given in Table 2.

The observed (image) color and the Hunter coordinates of mixtures of the green-yellow color-formers of this invention with N-(monosubstituted)dithiooxamides and N,N'-(disubstituted)dithiooxamides are noted in Experiments 4, 5, and 6, and Tables 3 and 4 below. Magenta and cyan color-formers described in U.S. patent application Ser. No. 07/473,776 have been found to be particularly effective when used in admixture with the green-yellow color-formers of this invention. Examples of such magenta and cyan color-formers that may be employed are shown below. The compounds shown below are exemplary only and are not to be considered limiting.

| | Magenta Color-formers |
|---|---|
| A | N,N'-di(2-octanoyloxyethyl)dithiooxamide |
| B | N,N'-di(dodecyl)dithiooxamide |
| C | N,N'-di(2-decanoyloxyethyl)dithiooxamide |
| D | N,N'-di(2-dodecanoyloxyethyl)dithiooxamide |
| E | N,N'-di(2-octanoylamidoethyl)dithiooxamide |
| F | N,N'-di(6-propanoylamidohexyl)dithiooxamide |
| G | N,N'-di(5-octanoylamido-2-methylpentyl)dithiooxamide mixed with N-(5-octanolyamido-2-methylpentyl)-N'-(5-octanoylamido-4-methylpentyl)dithiooxamide and N,N'-di(5-octanolyamido-4-methylpentyl)dithiooxamide |
| H | N,N'-di(benzyl)dithiooxamide |
| I | N,N'-di(benzoyloxyethyl)dithiooxamide |
| | Cyan Colorformers |
| A' | N-(2-octanoyloxyethyl)dithiooxamide |
| B' | N-dodecyldithiooxamide |
| C' | N-(2-decanoyloxyethyl)dithiooxamide |
| D' | N-(2-dodecanoyloxyethyl)dithiooxamide |
| E' | N-(2-octanoylamidoethyl)dithiooxamide |
| F' | N-(6-propanoylamidohexyl)dithiooxamide |
| G' | N-(5-octanoylamido-2-methylpentyl)dithiooxamide mixed with N-(5-octanolyamido-4-methylpentyl)dithiooxamide |

EXPERIMENTAL EXAMPLES

As the following experiments show, according to the present invention, there is defined a class of color-formers defined by structure I useable in the formation of a green-yellow complex upon association with a transition metal cation. The complex is not only of the preferred color, but also the class of compounds according to the invention is relatively nonvolatile and thus readily useable in products for which a green-yellow component of the image is preferred, such as carbonless paper constructions.

Experiment 1

Preparation of
2,5-bis(o-hydroxyphenyl)thiazolo[5,4-d]thiazole-Compound 1

Into a 100 ml round bottomed flask equipped with heating mantle and magnetic stirrer, were added 2.0 g (0.017 mol) of dithiooxamide (DTO) and 21 g (0.17 mol—a tenfold excess) of o-hydroxybenzaldehyde (salicylaldehyde). The salicylaldehyde was purchased from Eastman Organic Chemicals Division of Eastman Kodak Company, Rochester, N.Y. The mixture was stirred and heated at 180°–185° C. for 2 hr. At 160° C. water began to boil off. After 2 hr, the reaction mixture was cooled to room temperature and 50 ml of ethanol/ether 1:1 were added. Stirring for 10 min was followed by filtration to remove the product. The product was washed with ethanol and dried in air overnight to afford 2.9 g (50%) of 2,5-bis(o-hydroxyphenyl)-thiazolo[5,4-d]thiazole, mp 300° C. NMR and IR were in agreement with the assigned structure.

Experiment 2

Preparation of
2,5-bis(3,5-di-t-butylsalicylidene)thiazolo[5,4-d]thiazole-Compound 2

Into a 100 ml round bottomed flask equipped with heating mantle and magnetic stirrer, were added 30 ml of dimethylformamide (DMF), 1.92 g (0.016 mol) of dithiooxamide (DTO) and 7.72 g (0.033 mol) of 3,5-di-t-butylsalicylaldehyde. The 3,5-di-t-butyl-salicylaldehyde was prepared as described by Casnati (see G. Casnati, et al., U.S. Pat. No. 4,151,201 incorporated herein by reference). The solution was heated at reflux for 1 hr. As the reaction progressed, the product began to precipitate. Upon cooling, the product was filtered off, washed with ethanol and dried in air for 24 hr to afford 4.0 g (0.0072 mol; 42%) of 2,5-bis(3,5-di-t-butyl-salicylidene)thiazolo[5,4-d]thiazole.

A 1% solution of the condensation product in the encapsulation fill mix was swabbed onto 3M carbonless paper blue/purple CF sheet containing a $nickel^{2+}$ salt (sold by the 3M Co. St. Paul, Minn.) with a cotton swab. The reflectance spectra had Hunter coordinates of:

L=88.13
a=−7.84
b=31.70

This color observed on the CF sheet was green-yellow. The ligand is stable in 1N hydrochloric acid, thus demonstrating its usefulness in urea-formaldehyde encapsulation processes. It does not form color when reacted with zinc rosinate. Solubility in a solvent blend of tributyl phosphate, diethyl phthalate and cyclohexane (capsule solvents for preparing carbonless copy-paper) was >9% by weight. Thus the ligand is eminently suitable for encapsulation. The ligand is not volatile at 71° C. overnight.

Experiment 3

Preparation of
2,5-(diphenyl)thiazolo[5,4-d]thiazole-Compound 3

2,5-(diphenyl)thiazolo[5,4-d]thiazole was prepared from dithiooxamide and benzaldehyde. Benzaldehyde was purchased from Aldrich Chemical Company, Milwaukee, Wis.

A 1% solution of the condensation product in a solvent blend of tributyl phosphate, diethyl phthalate and cyclohexane (capsule solvents for preparing carbonless copy-paper) was swabbed onto a carbonless paper CF sheet (sold by the 3M Co. St. Paul, Minn.) with a cotton swab. There was no observed color on the CF.

Experiment 4

Preparation of Other 2,5-bis(substituted aryl)thiazolo[5,4-d]thiazoles

In a manner similar to that described above, the following 2,5-disubstituted-thiazolo[5,4-d]thiazole compounds were prepared:

Compound 4: 2,5-bis(furyl)thiazolo[5,4-d]thiazole was prepared from dithiooxamide and 2-furaldehyde. 2-furaldehyde (furfural) was purchased from Aldrich Chemical Company, Milwaukee, Wis.

Compound 5: 2,5-bis(2-methoxyphenyl)thiazolo[5,4-d]thiazole was prepared from dithiooxamide and o-methoxybenzaldehyde. o-Methoxybenzaldehyde was purchased from Aldrich Chemical Company, Milwaukee, Wis.

Compound 6: 2,5-bis(2-hydroxy-3-allylphenyl)-thiazolo[5,4-d]thiazole was prepared from dithiooxamide and 2-hydroxy-3-allylbenzaldehyde. 2-Hydroxy-3-allylbenzaldehyde was purchased from Frinton Chemical Company, Vineland, N.J. The color of this color-former on a CF sheet was green-yellow. The ligand is stable in 1N hydrochloric acid, and does not form color when reacted with zinc rosinate. Solubility in a solvent blend of tributyl phosphate, diethyl phthalate and cyclohexane (capsule solvents for preparing carbonless copy-paper) was 2% by weight. Thus the ligand is eminently suitable for encapsulation. The ligand is not volatile at 71° C. overnight.

Compound 7: 2,5-bis(2-hydroxy-3-methoxyphenyl)-thiazolo[5,4-d]thiazole was prepared from dithiooxamide and 2-hydroxy-3-methoxybenzaldehyde (o-vanillin). 2-Hydroxy-3-methoxybenzaldehyde was purchased from Aldrich Chemical Company, Milwaukee, Wis.

Compound 8: 2,5-bis(3,5-di-t-butyl-4-hydroxyphenyl)thiazolo[5,4-d]thiazole was prepared from dithiooxamide and 3,5-di-t-butyl-4-hydroxybenzaldehyde. 3,5-Di-t-butyl-4-hydroxybenzaldehyde was purchased from Aldrich Chemical Company, Milwaukee, Wis.

Experiment 5

Preparation of Black Image

A mixture of 20% by weight of compound (1), 10% N,N'-di(benzyl)dithiooxamide (H), and 70% N,N'-di(2-octanoyloxyethyl)dithiooxamide (A) was dissolved in a mixture of diethyldodecanamide:cyclohexane (50:50 ratio by weight) so that the percent solids was 1%. A cotton swab of the solution was wiped onto a CF sheet and the resulting image had the Hunter coordinates as follows:

L=55.56
a=1.92
b=3.02

The L value indicates the image is dark and has good contrast on a light background. The values of a and b indicate the image is black.

A mixture of 30% by weight of compound (1), 10% N,N'-di(benzyl)dithiooxamide (H), and 60% N,N'-di(2-octanoyloxyethyl)dithiooxamide (A) was dissolved in a mixture of diethylphthalate:cyclohexane (50:50 ratio by weight) so that the percent solids was 1%. A cotton swab of the solution was wiped onto a CF sheet and the resulting image had the Hunter coordinates as follows:

L=53.42
a=2.80
b=1.09

The L value indicates the image is dark and has good contrast on a light background. The values of a and b indicate the image is black.

A mixture of 20% by weight of compound (1), 30% N,N'-di(2-octanoyloxyethyl)dithiooxamide (A) and 20% N-dodecyldithiooxamide (B') was dissolved in a mixture of butyl diglyme:benzylbenzoate:cyclohexane (38:12:50 ratio by weight) so that the percent solids was 1%. A cotton swab of the solution was wiped onto a CF sheet and the resulting image had the Hunter coordinates as follows:

L=49.63
a=−3.02
b=−3.21

The L value indicates the image is dark and has good contrast on a light background. The values of a and b indicate the image is greenish-black.

Experiment 6

Encapsulation of 2,5-bis(substituted aryl)thiazolo[5,4-d]thiazole Color-Formers Compounds and Preparation of the CB Sheet A precondensate solution was prepared comprising 192 g of formalin, 0.63 g of potassium tetraborate, 72 g of urea, and 328 g of soft water. The formalin was 37% formaldehyde and was added to a 1-liter flask equipped with a stirrer and heating mantle. The potassium tetraborate and urea were then added, and the mixture was heated to 70° C. The reaction was maintained at that temperature for 2.5–3.0 hr. The reaction mixture was then diluted with the water and allowed to cool. The precondensate solution, with about 24% solids, was then ready for use in the encapsulation process.

The precondensate color-formers and carrier (e.g., fill solvents) were combined to make capsules according to the following procedure. Sodium chloride (29.54 g) was added to the stirred precondensate solution and the temperature of the solution was adjusted to 20° C. The fill material (215 g) was added and full agitation was begun. The fill solution consisted of 5% of a color-former mixture of Compound 1 (25%), Compound A (50%), and Compound H (25%) and 95% of a solvent mixture of diethyldodecanamide (67%) and cyclohexane (33%). After 5 minutes of stirring, 10% hydrochloric acid solution was added over 5 minutes in an amount such that the final pH of the reaction mixture was about 2.8. The reaction mixture was stirred for another 12 minutes. More of the 10% hydrochloric acid solution was added over a period of 12 minutes, in an amount such that the final pH of the solution was about 1.8. The reaction mixture was stirred at 20° C. for 1 hr, and then at 60° C. for 1–3 hr. The acidic solution was allowed to cool and adjusted to a pH of 7 by addition of concentrated ammonium hydroxide solution (28%). The capsule slurry could then be stored for later use.

The capsule slurry (10 g) was added to 65 g of a 1.5% aqueous sodium alginate solution. The mixture was applied to a coated paper using a bar coater with a 3 mil (76 μm) gap. The coating was allowed to dry at room temperature. The coated sheet was neutral in color and when imaged with a CF sheet coated with a nickel$^{2+}$ salt, an immediate image was formed with Hunter coordinates of:

L = 62.91
a = −0.27
b = 3.14

Experiment 7
Formation of Dark Images by Blending of Capsules

A 2% solution of compound 1 in a capsule fill solvent of N,N-diethyltoluamide was encapsulated by the procedure described in Experiment 6 above to form a capsule slurry of green-yellow color-former. A second fill solution consisting of 11.5% of Compound A (10%) and Compound H (1.5%) and 88.5% of a solvent mixture of butyl diglyme (38%), benzyl benzoate (12%) and cyclohexane (50%) was also encapsulated as described in Experiment 6 above to form a capsule slurry of magenta (blue/purple) color-former. A coating mixture of 10 g of each capsule slurry, and 62.5 g of 1.5% sodium alginate solution was coated onto paper by the draw down procedure described in Experiment 6 above. The thus formed CB sheet was neutral in color and when imaged with a 3M Carbonless Paper Blue/Purple CF sheet coated with a nickel$^{2+}$ salt, an immediate image was formed with Hunter coordinates of:

L = 58.61
a = 3.60
b = 5.31

The image appeared reddish black to the eye. The L value indicates the image is dark and has good contrast on a light background. The values for a and b indicate the image is reddish black.

The invention has been described with reference to various specific and preferred embodiments and techniques. It should be understood, however, that many variations and modifications may be made while remaining within the spirit and scope of the invention.

TABLE 1
Representative 2,5-bis(substitutedaryl)thiazolo[5,4-d]thiazoles

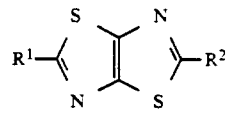

| Ref. No. | R$^1$ | R$^2$ | m.p.[1] | m.p. (lit)[2] |
|---|---|---|---|---|
| 1 | 2-hydroxyphenyl | 2-hydroxyphenyl | 300° C. | 300° C. |
| 2 | 2-hydroxy-3,5-di-t-butylphenyl | 2-hydroxy-3,5-di-t-butylphenyl | 228° C. | new compound |
| 3 | phenyl | phenyl | 211° C. | 209–210° C. |
| 4 | 2-furyl | 2-furyl | 238–240° C. | 241° C. |
| 5 | 2-methoxyphenyl | 2-methoxyphenyl | 253–254° C. | 254° C. |
| 6 | 2-hydroxy-3-allylphenyl | 2-hydroxy-3-allyphenyl | 203° C. | new compound |
| 7 | 2-hydroxy-3-methoxyphenyl | 2-hydroxy-3-methoxyphenyl | 290° C. | new compound |
| 8 | 4-hydroxy-3,5-di-t-butylphenyl | 4-hydroxy-3,5-di-t-butylphenyl | 308° C. | new compound |

[1] All melting points are uncorrected and were taken on a Thomas Hoover Capillary Melting Point Apparatus (Arthur H. Thomas Co., Philadelphia, Pa.)
[2] Johnson, J. R. and Ketcham, R. J. Amer. Chem. Soc. 1960, 82, 2719.

TABLE 2
Color Coordinates of Ni(II) Complexes of Green-Yellow Color-formers

| Compound No.* | Dye Conc.** | Color on CB | Image Color | Hunter Coordinates L | a | b |
|---|---|---|---|---|---|---|
| Solvent Mixture of Diethylphthalate:Tributylphosphate (50:50) | | | | | | |
| 1 | 1.0% | Colorless | Green-Yellow | 85.5 | −14.9 | 43.4 |
| Solvent Mixture of Diethylphthalate:Tributylphosphate:Cyclohexane (27:17:55) | | | | | | |
| 1 | 1.0% | Colorless | Green-Yellow | 88.7 | −14.9 | 37.2 |
| Solvent Mixture of N,N-Diethyldodecanamide:Cyclohexane (50:50) | | | | | | |
| 1 | 1.0% | Colorless | Green-Yellow | 87.0 | −14.7 | 38.2 |
| Solvent Mixture of Butyl Diglyme:Benzyl Benzoate:Cyclohexane (38:12:50) | | | | | | |
| 1 | 1.0% | Colorless | Green-Yellow | 87.3 | −13.8 | 34.7 |
| Solvent Mixture of Diethylphthalate:Cyclohexane (50:50) | | | | | | |
| 1 | 1.0%*** | Colorless | Green-Yellow | 87.5 | −12.3 | 30.8 |
| 2 | 1.0% | Colorless | Green-Yellow | 82.7 | −7.0 | 34.7 |
| 3 | 1.0% | Colorless | Colorless | | | |
| 4 | 1.0% | Colorless | Colorless | | | |
| 5 | 1.0% | Colorless | Colorless | | | |
| 6 | 1.0% | Colorless | Green-Yellow | 87.8 | −15.4 | 35.4 |
| 7 | 1.0% | Colorless | Green-Yellow | 89.5 | −15.6 | 36.1 |
| 8 | 1.0% | Colorless | Colorless | | | |
| Compounds from D. R. Yarian [U.S. Pat. No. 4,334,015 (1982)]: | | | | | | |
| 20 | 1.0% | Yellow | Green-Yellow | 86.9 | −13.2 | 35.5 |
| 21 | 1.0% | Yellow | Green-Yellow | 88.7 | −14.5 | 33.4 |

*See Table 1 for molecular structures
**Dye Concentration
***Did not all dissolve in this solvent mixture

TABLE 3
Color Coordinates of Ni(II) Complexes of Mixtures of Green-Yellow Color-Formers with N,N'-(Disubstituted)dithiooxamide Color-formers

| Weight Ratio | Class of Compound** | Ref. No. | *Dye Conc. | Image Color | Hunter Coordinates L | a | b |
|---|---|---|---|---|---|---|---|
| 20% | Yellow Color-former | 1 | 5% | Red-Black | 38.5 | 8.4 | −1.8 |
| 70% | Magenta Color-former | A | | | | | |
| 10% | Magenta Color-former | H | | | | | |
| 20% | Yellow Color-former | 1 | 5% | Blue-Black | 36.2 | 7.0 | −4.6 |

TABLE 3-continued

Color Coordinates of Ni(II) Complexes of Mixtures of Green-Yellow Color-Formers with N,N'-(Disubstituted)dithiooxamide Color-formers

| Weight Ratio | Class of Compound** | Ref. No. | *Dye Conc. | Image Color | Hunter Coordinates L | a | b |
|---|---|---|---|---|---|---|---|
| 60% | Magenta Color-former | A | | | | | |
| 20% | Magneta Color-former | H | | | | | |
| 25% | Yellow Color-former | 1 | 5% | Neutral-Black | 37.2 | −5.3 | −3.5 |
| 50% | Magenta Color-former | A | | | | | |
| 25% | Magenta Color-former | H | | | | | |
| 0% | Yellow Color-former | none | 5% | Blue-Purple | 34.3 | 12.0 | −15.2 |
| 75% | Magenta Color-former | A | | | | | |
| 25% | Magenta Color-former | H | | | | | |

*Dye Concentration
**See Table 1 for molecular structures of Yellow Color-formers

TABLE 4

Color Coordinates of Ni(II) Complexes of Mixtures of Green-Yellow Color-Formers with N,N'-(disubstituted)dithiooxamide Color-formers in Various Fill Solvents

| Weight Ratio | Class of Compound** | Ref. No. | *Dye Conc. | Image Color | Hunter Coordinates L | a | b |
|---|---|---|---|---|---|---|---|
| Solvent Mixture of Diethyl Phthalate:Cyclohexane (50:50) | | | | | | | |
| 0% | Yellow Color-former | 1 | 1% | Blue-Purple | 58.2 | 10.2 | −11.5 |
| 85% | Magenta Color-former | A | | | | | |
| 15% | Magenta Color-former | H | | | | | |
| 10% | Yellow Color-former | 1 | 1% | Blue-Purple | 60.4 | 5.7 | −3.8 |
| 75% | Magenta Color-former | A | | | | | |
| 15% | Magneta Color-former | H | | | | | |
| 20% | Yellow Color-former | 1 | 1% | Red-Black | 56.3 | 5.0 | −2.8 |
| 70% | Magenta Color-former | A | | | | | |
| 10% | Magenta Color-former | H | | | | | |
| 30% | Yellow Color-former | 1 | 1% | Black | 53.4 | 2.8 | 1.1 |
| 60% | Magenta Color-former | A | | | | | |
| 10% | Magenta Color-former | H | | | | | |
| Solvent Mixture of Butyl Diglyme:Benzyl Benzoate:Cyclohexane (38:12:50) | | | | | | | |
| 0% | Yellow Color-former | 1 | 1% | Blue-Purple | 58.5 | 8.8 | −12.9 |
| 85% | Magenta Color-former | A | | | | | |
| 15% | Magenta Color-former | H | | | | | |
| 10% | Yellow Color-former | 1 | 1% | Blue-Purple | 59.7 | 6.1 | −7.9 |
| 75% | Magenta Color-former | A | | | | | |
| 15% | Magneta Color-former | H | | | | | |
| 20% | Yellow Color-former | 1 | 1% | Blue-Black | 58.7 | 4.8 | −7.5 |
| 70% | Magenta Color-former | A | | | | | |
| 10% | Magenta Color-former | H | | | | | |
| 30% | Yellow Color-former | 1 | 1% | Black | 57.7 | 1.7 | 0.2 |
| 60% | Magenta Color-former | A | | | | | |
| 10% | Magenta Color-former | H | | | | | |
| Solvent Mixture of Diethyldodecanamide:Cyclohexane (50:50) | | | | | | | |
| 0% | Yellow Color-former | 1 | 1% | Blue-Purple | 70.2 | 8.2 | −10.5 |
| 85% | Magenta Color-former | A | | | | | |
| 15% | Magenta Color-former | H | | | | | |
| 10% | Yellow Color-former | 1 | 1% | Blue-Purple | 59.2 | 6.1 | −6.0 |
| 75% | Magenta Color-former | A | | | | | |
| 15% | Magneta Color-former | H | | | | | |
| 20% | Yellow Color-former | 1 | 1% | Black | 55.6 | 1.9 | −3.0 |
| 70% | Magenta Color-former | A | | | | | |
| 10% | Magenta Color-former | H | | | | | |
| 30% | Yellow Color-former | 1 | 1% | Olive | 59.7 | −0.4 | 7.9 |
| 60% | Magenta Color-former | A | | | | | |
| 10% | Magenta Color-former | H | | | | | |
| Solvent Mixture of N,N-Diethyl-m-toluamide:Cyclohexane (50:50) | | | | | | | |
| 20% | Yellow Color-former | 1 | 2% | Reddish-Black | 50.9 | 6.5 | 2.2 |
| 70% | Magenta Color-former | A | | | | | |
| 10% | Magenta Color-former | H | | | | | |
| 20% | Yellow Color-former | 1 | 2% | Reddish-Black | 44.8 | 7.1 | −1.1 |
| 60% | Magenta Color-former | A | | | | | |
| 20% | Magneta Color-former | H | | | | | |
| 25% | Yellow Color-former | 1 | 2% | Black | 48.9 | 4.8 | −3.3 |
| 50% | Magenta Color-former | A | | | | | |
| 25% | Magenta Color-former | H | | | | | |
| 30% | Yellow Color-former | 1 | 2% | Brownish-Black | 52.4 | 4.6 | 8.5 |
| 50% | Magenta Color-former | A | | | | | |
| 20% | Magenta Color-former | H | | | | | |

*Dye Concentration
**See Table 1 for molecular structures of Yellow Color-formers

I claim:

1. A microcapsule containing a composition capable of forming colored complexes with transition metal salts, said composition comprising a 2,5-bis-(substituted aryl)thiazolo[5,4-d]thiazole compound carried in an organic cosolvent vehicle, said compound having the formula:

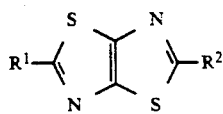

wherein R¹ is an ortho-hydroxy-substituted aryl group and R² is an aryl group of hydrogen.

2. The microcapsule of claim 1 wherein R¹ is selected from the group consisting of o-hydroxy phenyl group and o-hydroxy naphthyl group, and R² is selected from the group consisting of phenyl group and naphthyl group.

3. The microcapsule of claim 1 wherein R¹ is selected from o-hydroxy phenyl group and o-hydroxy naphthyl group and R² is selected from o-hydroxy phenyl group and o-hydroxy naphthyl group.

4. A microcapsule according to claim 1 wherein said 2,5-bis-(substituted aryl)thiazolo[5,4-d]thiazole compound is present in said cosolvent in an amount of between 0.2 and 10.0 percent by weight of the capsule fill.

5. The microcapsule of claim 1 wherein an N-(monosubstituted)dithiooxamide, an N,N'-(disubstituted)dithiooxamide, or a mixture thereof, is also contained in the organic cosolvent vehicle.

6. The microcapsule of claim 1 wherein said 2,5-bis-(substituted aryl)thiazolo[5,4-d]thiazolo is represented by

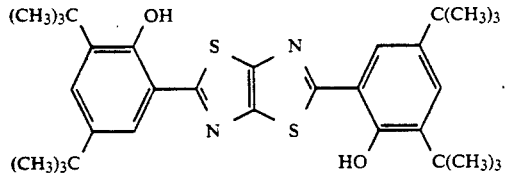

7. The microcapsule of claim 1 wherein said 2,5-bis-(substituted aryl)thiazolo[5,4-d]thiazole is represented by the formula:

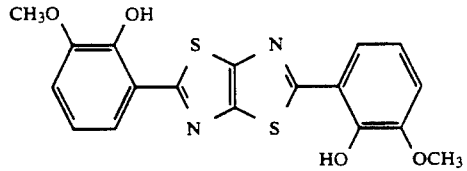

8. The microcapsule of claim 1 wherein said 2,5-bis-(substituted aryl)thiazolo[5,4-d]thiazolo is encapsulated in a substantially impermeable, pressure-rupturable microcapsule.

9. The microcapsule of claim 8 wherein said encapsulated compound is present in said cosolvent in an amount of between 0.2 and 10.0 percent by weight of the capsule fill.

10. A substrate comprising a surface on which is coated an encapsulated 2,5-bis(substituted aryl)-thiazolo[5,4-d]thiazole compound in a solvent, said compound having the formula:

wherein R¹ is o-hydroxy aryl group; and R² is an aryl group.

11. A construction comprising:
(a) a first substrate with a surface on which is coated a 2,5-bis(substituted aryl)thiazolo[5,4-d]thiazole color-forming compound of the formula:

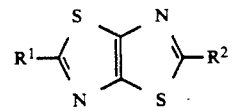

wherein R¹ is an o-hydroxy substituted aryl group; and R², is selected from the group of substituents consisting of an aryl group and hydrogen;
(b) a second substrate with a surface on which is coated a salt of a transition metal cation with a +2 oxidation state, wherein said second substrate surface is juxtaposed in contact with said coated surface of said first substrate; and
(c) means for separating said color-forming compound from reaction with said transition metal cation until said construction is subjected to activating pressure.

12. The construction according to claim 11 wherein the 2,5-bis(substituted aryl)thiazolo[5,4-d]thiazole color-forming compound is represented by the formula

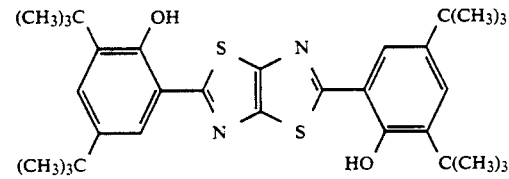

13. The construction according to claim 11 wherein the 2,5-bis(substituted aryl)thiazolo[5,4-d]thiazole color-forming compound is represented by the formula:

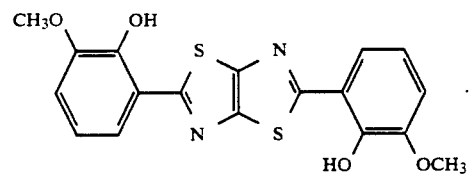

14. The construction according to claim 11 wherein said surface of said first substrate, which is coated with a 2,5-bis(substituted aryl)thiazolo[5,4-d]thiazole color-forming compound is also coated with an N-(monosubstituted)dithiooxamide, an N,N'-(disubstituted)dithiooxamide, or a mixture thereof.

15. The construction according to claim 11 wherein said 2,5-bis(substituted aryl)thiazolo[5,4-d]thiazole color-forming compound is encapsulated in a substantially impermeable, pressure-rupturable microcapsule.

16. The construction according to claim 15 wherein said surface of said first substrate, which is coated with an encapsulated 2,5-bis(substituted aryl)thiazolo[5,4-d]thiazole color-forming compound is also coated with an encapsulated N-(monosubstituted)dithiooxamide, an N,N'-(disubstituted)dithiooxamide, or a mixture thereof.

17. The construction according to claim 15 wherein said surface of said first substrate, is coated with an encapsulated 2,5-bis(o-hydroxyaryl)thiazolo[5,4-d]thiazole mixed with an N-(monosubstituted)dithiooxamide, an N,N'-(disubstituted)dithiooxamide, or a mixture of an N-(monosubstituted)dithiooxamide and an N,N'-(disubstituted)dithiooxamide.

18. The construction according to claim 11 wherein said construction comprises:
   (a) a plurality of first surfaces, each of which is coated with a 2,5-bis-(o-hydroxyaryl)thiazolo[5,4-d]thiazole color-forming compound;
   (b) a plurality of second surfaces, each of which is coated with the transition metal salt; and wherein
   (c) each of said coated first surfaces is juxtaposed in contact with one each of said coated second surfaces so as to form a stock.

19. The construction according to claim 18 wherein said surface of said first substrate, which is coated with a 2,5-bis(o-hydroxyaryl)thiazolo[5,4-d]thiazole color-forming compound is also coated with an N-(monosubstituted)dithiooxamide, an N,N'-(disubstituted)dithiooxamide, or a mixture thereof.

20. A method of forming an image on a receptor sheet; said method comprising:
   (a) providing a receptor sheet comprising a surface with a transition metal salt coated thereon; and
   (b) transferring to said coated surface of the receptor sheet an effective amount of a 2,5-bis(o-hydroxyaryl)thiazolo[5,4-d]thiazole color-forming compound of formula:

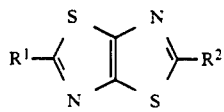

wherein R¹ is an o-hydroxy substituted phenyl or o-hydroxy naphthyl group; and R², is selected from the group of substituents consisting of an aryl group and hydrogen.

21. The method according to claim 20 wherein said step of transferring comprises:
   (a) providing a donor sheet comprising a surface with said color forming compound encapsulated in microcapsules and coated thereon;
   (b) placing said coated surface of the donor sheet in contact with said coated surface of the receptor sheet; and
   (c) applying activating pressure to said donor sheet sufficient to break the microcapsules and release the encapsulated compound for transfer to said receptor sheet.

22. The method according to claim 20 wherein said step of transferring further comprises transferring an N-(monosubstituted)dithiooxamide compound, an N,N'-(disubstituted)dithiooxamide compound, or a mixture thereof, to the coated surface, along with the effective amount of 2,5-bis(o-hydroxyaryl)thiazolo[5,4-d]thiazole compound.

23. The method according to claim 20 wherein said color-forming compound is represented by the formula:

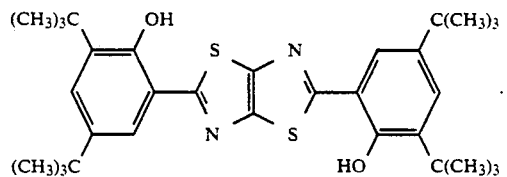

24. The method according to claim 20 wherein said color-forming compound is represented by the formula:

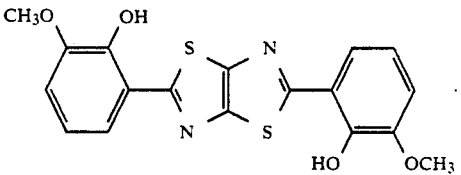

* * * * *

UNITED STATES PATENT AND TRADEMARK OFFICE
CERTIFICATE OF CORRECTION

PATENT NO.: 5,284,812

DATED: February 8, 1994

INVENTOR(S): Jubran

It is certified that error appears in the above-identified patent and that said Letters Patent is hereby corrected as shown below:

Column 7, line 65, delete "described" and insert --describe--.

Column 7, line 67, after the word "color-formers" and before the word "and", insert --is employed--.

Column 11, line 25, delete "Then" and insert --When--.

Column 25, line 33, delete "aryl)thiazolo[5,4-d]thiazolo" and insert --aryl)thiazolo[5,4-d]thiazole--.

Column 25, line 57, delete "aryl)thiazolo[5,4-d]thiazolo" and insert --aryl)thiazolo[5,4-d]thiazole--.

Column 27, line 23, delete "stock" and insert --stack--.

Signed and Sealed this

Eleventh Day of June, 1996

Attest:

BRUCE LEHMAN

*Attesting Officer*  *Commissioner of Patents and Trademarks*